United States Patent [19]

Clark

[11] 4,299,303

[45] Nov. 10, 1981

[54] NOISE ATTENUATING STETHOSCOPE

[76] Inventor: Thomas W. Clark, 611 Westwinds Dr., Palm Harbor, Fla.

[21] Appl. No.: 131,901

[22] Filed: Mar. 20, 1980

[51] Int. Cl.³ .............................................. A16B 7/02
[52] U.S. Cl. .................................. 181/131; 181/135; 181/137
[58] Field of Search ...................... 181/131, 135, 137; 73/585, 591, 649; 179/107; 16/2; 2/209

[56] References Cited

U.S. PATENT DOCUMENTS

| 885,836 | 4/1908 | Bullock, Jr. | 16/2 X |
|---|---|---|---|
| 1,203,329 | 11/1916 | Heck | 73/591 |
| 1,738,094 | 12/1929 | Caldwell et al. | 73/591 |
| 3,321,041 | 5/1967 | Bowen | 181/131 |
| 3,455,293 | 7/1969 | Bethune | 181/131 |
| 3,469,651 | 9/1969 | Mendelson et al. | 181/135 |
| 3,543,875 | 12/1970 | Littmann | 181/137 |
| 3,686,691 | 8/1972 | Anderson | 2/209 |
| 3,837,681 | 9/1974 | Reynolds | 181/131 |
| 4,149,610 | 4/1979 | Saiya et al. | 181/131 |

FOREIGN PATENT DOCUMENTS 2844147 4/1979 Fed. Rep. of Germany ...... 181/131

Primary Examiner—L. T. Hix
Assistant Examiner—Thomas H. Tarcza
Attorney, Agent, or Firm—Duckworth, Allen, Dyer & Pettis

[57] ABSTRACT

A noise attenuating stethoscope is coupled to a noise attenuating headset having first and second sound attenuating ear cups which are coupled to the ends of a headband. A pair of ear tubes extends laterally through an aperture in the side of each ear cup and includes an ear piece coupled to each end thereof. A resilient sealing device is positioned within the aperture of each ear cup and surrounds the outer surface of each ear tube to form a seal between the ear tubes and the ear cups to attenuate the transmission of sound through the apertures and for permitting the ear tubes to be both angularly deflected and laterally displaced with respect to the ear cups. A sound delivery tube couples a sound pick up to each of the ear tubes to transmit sound from the sound pick up to the ear tubes. The noise attenuating stethoscope may further include a quick-connect coupling between the sound pick up and the sound delivery tube.

6 Claims, 4 Drawing Figures

NOISE ATTENUATING STETHOSCOPE

BACKGROUND OF THE INVENTION

1. Field of the Invention

The present invention relates to noise attenuating stethoscopes, and more particularly, to noise attenuating stethoscopes having ear pieces which are angularly deflectable within the ear cups of the stethoscope.

2. Description of the Prior Art

The prior art discloses a wide variety of noise attenuating stethoscopes. U.S. Pat. No. 3,321,041, (Bowen) discloses a noise attenuating stethoscope which includes a noise attenuating headset having a pair of ear cups. A pair of sound delivery tubes transmit sounds from a sound pick up through the lower surface of the sound absorbing ear cups of the noise attenuating head set. An L-shaped ear tube extends vertically upward from the bottom of each ear cup and extends beyond the inner surface of each ear cup to engage an ear of the individual utilizing the device.

U.S. Pat. No. 3,837,681 (Reynolds) discloses a noise attenuating stethoscope which includes a threaded sleeve coupling each sound attenuating ear cup to permit independent lateral adjustment of each ear piece with respect to each cup. U.S. Pat. No. 350,393, (Ridzinsky) discloses a stethoscope having a pair of soft rubber, sound insulating cups, each of which includes a fixed ear piece for transmitting sounds from the stethoscope to the ear of the individual using the device.

U.S. Pat. No. 1,203,329, (Heck) discloses a stethoscope having two wound pick ups and a switching device for selectively coupling one of the sound pick ups to the ears of the individual listening to the device.

U.S. Pat. No. 3,686,691, (Anderson) discloses a noise attenuating headset of the type which the elements of the present invention are coupled. In order to supplement the following disclosure of the preferred embodiment of the present invention, U.S. Pat. No. 3,686,691, is hereby incorporated by reference.

SUMMARY OF THE INVENTION

The present invention contemplates a noise attenuating stethoscope which includes a noise attenuating headset having first and second sound attenuating ear cups which are coupled to the ends of the headband. A pair of ear tubes extend laterally through an aperture in the side of each ear cup and include an ear piece which is coupled to one end of each ear tube. Resilient sealing means is coupled within the aperture in each ear cup and surrounds the outer surface of each ear tube in order to form a seal between the ear tube and the ear cups to attenuate the transmission of sound through the apertures and to permit the ear tubes to be both angularly deflected and laterally displaced with respect to the ear cups. Sound delivery means is coupled to a sound pick up and to each of the ear tubes to transmit sound from the sound pick up to each ear tube.

Another embodiment of the present invention includes a pair of tubular ear pieces each of which is slidably displaceable with respect to the ear tubes. Biasing means is coupled to each of the ear pieces and to each of the ear tubes to bias the ear pieces out from the ear tubes.

In yet another embodiment of the present invention locking means are provided for fixing the relative position of each ear tube with respect to its corresponding sealing means. Finally, the noise attenuating stethoscope may further comprise a quick-connect coupling between the sound pick up and the sound delivery tube so as to allow monitoring of the patient by different personnel without the necessity of repositioning the sound pick up. This is, of course, most desirable in instances where the patient's pulse is extremely weak. By virtue of the quick-connect, a transfer of the monitoring operation from one individual to another may be accomplished in just a matter of seconds.

DESCRIPTION OF THE DRAWINGS

The invention is pointed out with particularity in the appended claims. However, other objects and advantages together with the operation of the invention may be better understood by reference to the following detailed description taken in connection with the following illustrations wherein:

DETAILED DESCRIPTION

Figure 1:
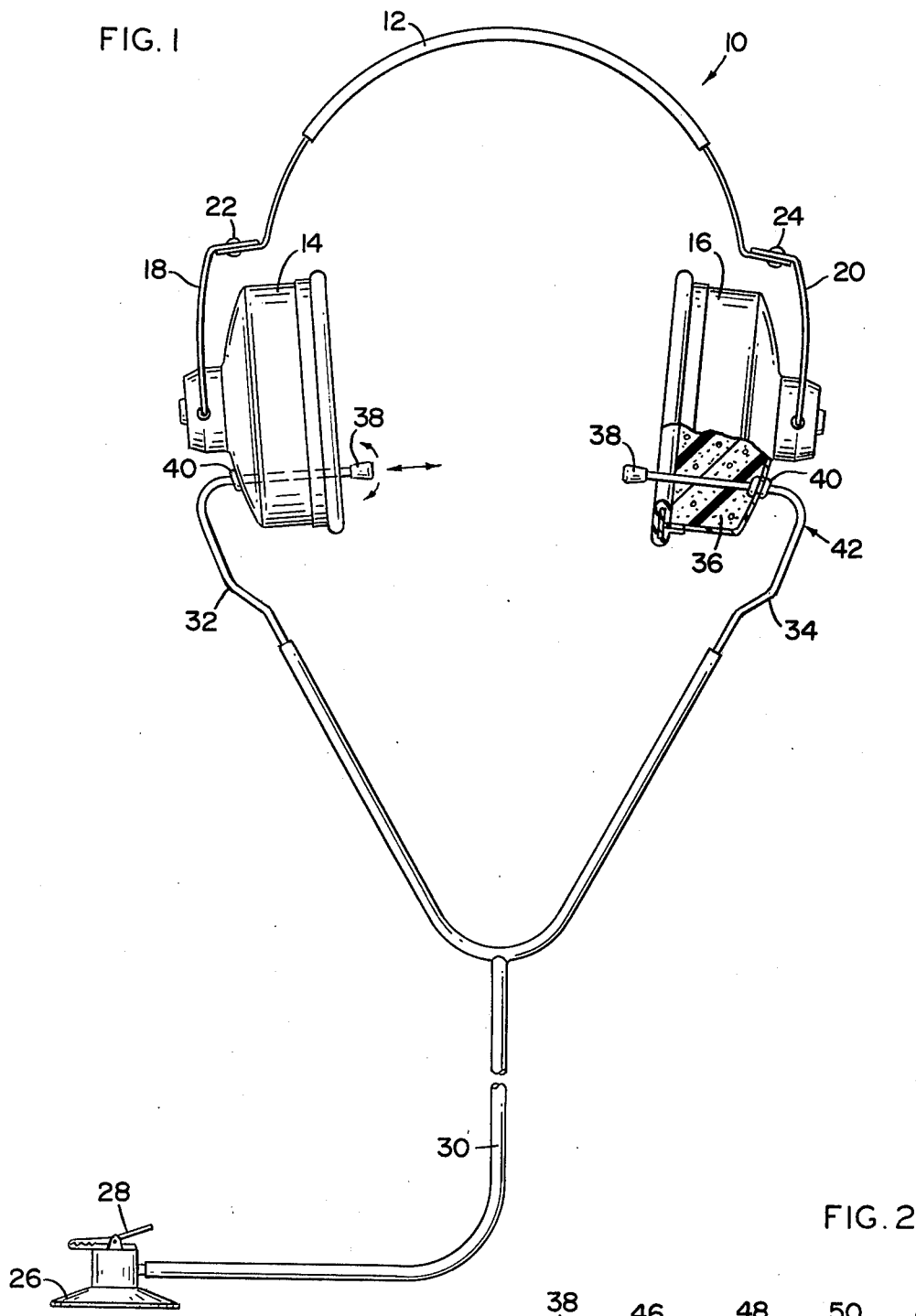
FIG. 1 is a front view, partially sectionalized, particularly illustrating a noise attenuating stethoscope in accordance with the present invention.

In order to better illustrate the advantages of the invention and its contributions to the art, a preferred hardware embodiment of the invention will now be described in some detail. Referring now to FIG. 1, the noise attenuating stethoscope of the present invention includes a noise attenuating headset 10 having a cushioned headband 12 and first and second sound attenuating ear cups 14 and 16. Headband 12 includes outer sections 18 and 20 which are rotatably coupled to headband 12 by securing means such as rivets 22 and 24. This three piece structural configuration for headband 12 permits side to side adjustment of the interface of cups 14 and 16 with respect to the head of the individual wearing the device. The lowermost portion of headband elements 18 and 20 extend around the outer portion of ear cups 14 and 16 and are rotatably coupled thereto to permit up and down adjustment of ear cups 14 and 16 with respect to the head of the wearer. The specific structure of the noise attenuating headset 10 is more fully described in U.S. Pat. No. 3,686,691, although any equivalent noise attenuating headset can be used in connection with the present invention.

A sound pick up 26 is of a conventional structure and may include a clip 28 for securing the sound pick up 26 to the clothing of the individual using the device. A Y-shaped conduit 30 is typically fabricated from a substantially rigid wall plastic material and includes a first end which is coupled to sound pick up 26 and second and third ends which are coupled to ear pieces 32 and 34. Sound delivery tube 30 transmits sound from sound pick up 26 to ear tubes 32 and 34.

Ear tubes 32 and 34 are typically made from hollow tubular sections of metal bent into the configuration illustrated. Each ear tube extends laterally through an aperture in the outer side surface of ear cups 14 and 16 and through foam plastic sound absorbing material 36. The exposed end of the ear tubes 32 and 34 each include a plastic ear piece 38 which is of conventional design and provides an air tight interface with the outer portion of the auditory canal of the wearer's ear.

Resilient sealing means 40, such as a rubber grommet, is positioned with the aperture in the outer sides of ear cups 14 and 16, and surrounds the outer surface of the ear tubes 32 and 34. Sealing means 40 forms a tight seal between ear tubes 32 and 34 and the external plastic shell of ear cups 14 and 16 to attenuate the transmission of sound through these apertures while simultaneously permitting ear tubes 32 and 34 to be both angularly deflected and laterally displaced with respect to ear cups 14 and 16. The arrows shown in the vicinity of the left hand ear piece 38 indicate that the generally horizontally oriented portion of ear tube 32 may be laterally displaced left and right with respect to ear cup 14 and may also be angularly deflected in any radial direction from the position illustrated in FIG. 1. This unique structure of the present invention thus permits ear piece 38 to precisely engage and be fitted to the auditory canal of any particular individual without the requirement for special fitting procedures.

Each ear piece includes a curved section designed by reference number 42 which is positioned outside of the external shell of ear cup 14 and 16. This curved section 42 orients the lower end of each ear tube with the upper end of Y-shaped conduit 30.

Figure 2:
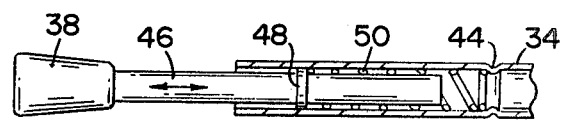
FIG. 2 illustrates a second embodiment of the noise attenuating stethoscope in which the ear tube and ear piece are slidably displaceable with respect to each other.

Referring now to FIG. 2, an embodiment of the present invention is disclosed which includes structure to facilitate lateral displacement of the ear pieces with respect to the ear tubes of the present invention. In this embodiment, a crimped section 44 is formed in the horizontally oriented portion of each ear tube to provide an inwardly extending cylindrical collar along the inner surface of ear tubes 32 and 34. An ear piece extension 46 is coupled to ear piece 38 and includes an outer diameter somewhat less than the inner diameter of ear tube 34. An outwardly extending collar 48 may be provided as shown along the exterior surface of ear piece extension 46. Biasing means in the form of a spring 50 has an outer diameter somewhat less than the inner diameter of ear tube 34 and an inner diameter somewhat greater than the outer diameter of ear piece extension 46. One end of spring 50 is retained in place by crimp 44 while the other end of spring 50 abuts collar 48. In this manner, spring 50 biases ear pieces 38 out from the ear tube to permit the lateral extension of each ear piece to readily be adjusted to fit into the auditory canal of the wearer. Stop pins may be provided instead of collars 44 and 48 or the ends of spring 50 may be directly coupled to the inner wall of ear piece 34 and to the outer wall of ear piece extension 46, to not only bias ear piece 38 outward from inner tube 34, but also to couple ear piece extension 46 to ear tube 34.

Figure 3:
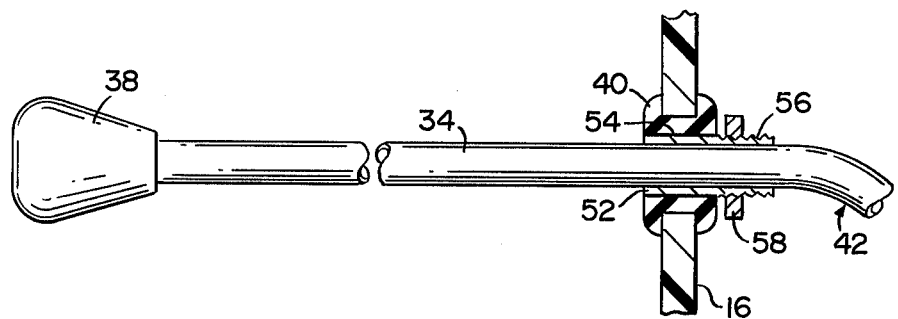
FIG. 3 is a sectional view of a third embodiment of the noise attenuating stethoscope in which the ear tube is slidably displaceable and further includes locking means for fixing the relative position of each ear tube with respect to its corresponding sealing means.

Attention is now invited to the view of FIG. 3 wherein a third embodiment of the noise attenuating stethoscope is shown. This third embodiment relates to locking means whereby the relative position of each ear tube 32 and 34 may be fixed with respect to its corresponding sealing means 40. As shown in the view of FIG. 3, a bushing 52 is fixedly attached within each resilient sealing means 40 as by cementing indicated at 54. Ear tube 34 is slidably displaceable within the bushing 52. Threads 56 are formed on the external end of bushing 52, and a lock nut 58 is operatively engaged with threads 56. The internal diameter of lock nut 58 is such that when it is tightened onto threads 56 a slight compression of bushing 52 will occur so that ear piece 34 is "locked" into position. Accordingly, by virtue of the locking means of this embodiment each of the ear pieces 32 and 34 may be fixed into proper lateral position for a particular user. Inasmuch as sealing means 40 are flexible, angular deflection of ear tubes 32 and 34 is still permitted.

Figure 4:
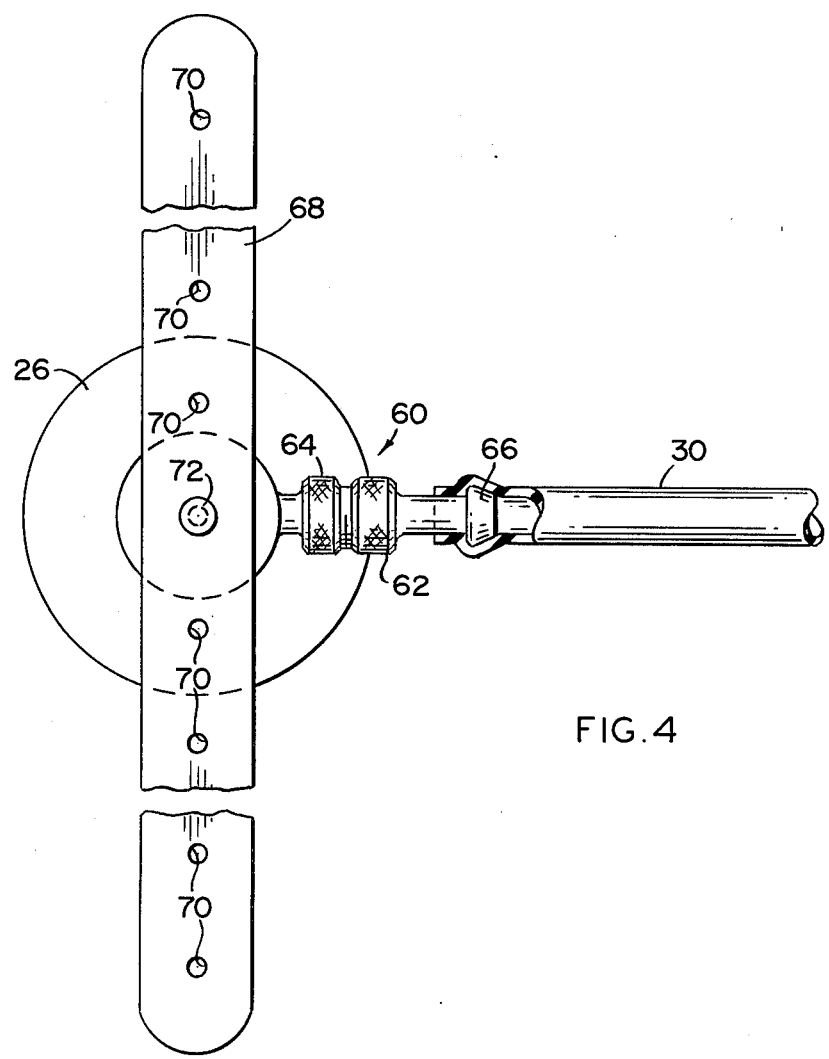
FIG. 4 is a plane view, partially in section, showing the quick-connect feature of the noise attenuating stethoscope.

Inasmuch as the noise attenuating stethoscope of the present invention is obviously intended for use in situations having relatively high background noise or a relatively low level patient heartbeat, placement of sound pick up 26 on the body of the patient is critical. If sound pick up 26 must be moved, as when changing the stethoscope from one user to another, or if sound pick up 26 is inadvertently moved, critical treatment time may be lost while searching for the heartbeat and repositioning sound pick up 26. In order to alleviate this problem the embodiment of FIG. 4 is provided. As can be seen in the plan view of FIG. 4, a sound pick up quick-connect, generally indicated as 60, is provided. Quick-connect 60 comprises a female member 62 and a male member 64. One end portion 66 of female member 62 is attached to sound delivery tube 30. Male member 64 is preferably integrally formed on sound pick up 26. A tapered female tip (not shown) formed on female member 62 in opposed relation to end portion 66 slidably engages a correspondingly configured aperture (not shown) formed through male member 64.

In order to provide for secure, relatively permanent placement of sound pick up 26 on the body of the patient, a strap 68 is provided. In the embodiment shown strap 68 is formed from an elastic material and includes a plurality of apertures 70 formed along its length. A tip 72 is formed at the top of sound pick up 26 in substantially perpendicular relation thereto, and tip 72 will extend through at least a pair of apertures 70 as when sound pick up 26 is placed on the arm of a patient and strap 68 is passed around the arm. By virtue of this construction strap 68 may be utilized to secure sound pick up 26 to the patient's body. It is to be understood that strap 68 need not necessarily formed from an elastic material as shown in the drawings. For example, an adjustable strap formed from fabric or other such material and including buckle or adjustment means might be utilized. In similar fashion, one end of the strap could be permanently affixed to sound pick up 26 and fastening means such as snaps, hooks or "Velcro" might be used. In any event, quick-connect 60 allows the entire headset and sound delivery tube of a noise attenuating stethoscope to be removed without the necessity of displacing sound pick up 26. Therefore, it is quite possible to change operators in a matter of one or two seconds. It is furthermore to be understood that the quick-connect means 60 may also be utilized in standard stethoscope constructions.

The unique structure of the present invention not only permits the stethoscope elements of the present invention to be readily adjusted both laterally and angularly to precisely fit the ears of the wearer, but also substantially reduces the ambient noise level perceived by the user of the device. It is thus possible for an emergency medical technician to listen to the very low level sounds which are transmitted through the stethoscope elements of the present invention to the ears. This is extremely important when the noise attenuating stethoscope of the present invention is utilized in crowded areas, in the vicinity of vehicular traffic, or to examine persons in other areas where the intensity of the noise is at such a high level that it is impossible to accurately diagnose a victim's condition as a result of noise interference.

It will be apparent to those skilled in the art that the disclosed noise attenuating stethoscope may be modified in numerous ways and may assume many embodiments other than the preferred forms specifically set out and described above. For example, numerous different types of noise attenuating headsets may be used in conjunction with the remaining structure of the present invention and numerous other materials other than the disclosed grommet may be used to function as the resilient sealing means described above. Accordingly, it is intended by the appended claims to cover all such modifications of the invention which fall within the true spirit and scope of the invention.

Now that the invention has been described, What is claimed is:

1. In a noise attenuating headset having first and second sound attenuating ear cups coupled to the end of a headband, a noise attenuating stethoscope comprising:
   a. A pair of ear tubes each having an ear piece coupled to a first end thereof, each of said ear tubes extending laterally through an aperture in the side of each ear cup;
   b. resilient swivel means disposed within the aperture and each ear cup and surrounding the outer surface of each ear tube for acoustically sealing said ear tubes and said ear cups and for coupling said ear tubes to the ear cups in an angularly deflectable and laterally displaceable mode;
   c. locking means mounted on each of said swivel means and operatively engageable with each of said ear tubes, said locking means comprising a bushing fixedly attached to said resilient swivel means and surrounding said outer surface of each of said ear tubes, a portion of said bushing extending outwardly from said ear cup, and moveable means engageable with said portion for compressing said portion into frictional engagement with said outer surface, whereby said ear tubes may be locked to prevent lateral displacement while still permiting angular deflection;
   d. a sound pick up; and
   e. a Y-shaped flexible conduit having a first end coupled to said sound pick up and second and third ends coupled to a second end of each ear tube.

2. The noise attenuating stethoscope of claim 1 wherein said resilient swivel means for acoustically sealing and coupling comprises a grommet.

3. The noise attenuating stethoscope of claim 2 wherein said grommet is fabricated from rubber.

4. The noise attenuating stethoscope of claim 1 further comprising quick-connect means operatively disposed in interconnecting relation between said sound pick up and said flexible conduit, whereby said sound pick up may be detached from said flexible conduit and means for securing said sound pick up to the article from which sounds are being monitored.

5. The noise attenuating stethoscope of claim 4 wherein said means for securing comprises a strap fabricated from an elastic material and having a plurality of apertures formed therethrough along the longitudinal dimension of said strap, and wherein said sound pick up comprises a tip formed thereon, said tip being dimensioned and configured to engage said strap by extending through at least one of said apertures when said straps is disposed in surrounding relation to said sound pick up and said article.

6. The noise attenuating stethoscope of claim 4 wherein said quick-connect means comprises a male member attached to said sound pick up in sound-transmitting relation thereto and a female member attached to a first end of said flexible conduit in sound-transmitting relation thereto, said male and female members being mateable one with the other.

* * * * *